(12) United States Patent
Polland et al.

(10) Patent No.: US 7,708,411 B2
(45) Date of Patent: May 4, 2010

(54) ONLINE WAVEFRONT MEASUREMENT AND DISPLAY

(75) Inventors: Hans-Joachim Polland, Wolfratshausen (DE); Gerhard Youssefi, Landshut (DE); Stefan Seitz, Germering (DE)

(73) Assignee: Bausch & Lomb Incorporated, Rochester, NY (US)

( * ) Notice: Subject to any disclaimer, the term of this patent is extended or adjusted under 35 U.S.C. 154(b) by 930 days.

(21) Appl. No.: 10/565,703

(22) PCT Filed: Jul. 22, 2004

(86) PCT No.: PCT/EP2004/008205

§ 371 (c)(1),
(2), (4) Date: Aug. 16, 2006

(87) PCT Pub. No.: WO2005/015495

PCT Pub. Date: Feb. 17, 2005

(65) Prior Publication Data
US 2007/0008491 A1    Jan. 11, 2007

(30) Foreign Application Priority Data
Jul. 24, 2003    (DE) .............................. 103 33 813

(51) Int. Cl.
*A61B 3/00* (2006.01)
(52) U.S. Cl. ...................................... 351/246
(58) Field of Classification Search ................. 351/205, 351/212, 246
See application file for complete search history.

(56) References Cited

U.S. PATENT DOCUMENTS

| 5,777,719 A | 7/1998 | Williams et al. |
| 6,234,631 B1 | 5/2001 | Sarver et al. |

FOREIGN PATENT DOCUMENTS

| DE | 42 22 395 A1 | 1/1994 |
| DE | 101 54 194 A1 | 5/2003 |
| DE | 600 04 020 T2 | 6/2004 |

OTHER PUBLICATIONS

Nirmaier T et al., *Hartmann-Shack sensor ASIC 's for real-time adaptive optics in biomedical physics*, 6th World Multiconference on Systemics, Cybernetics, and Informatics, vol. 13, 2002, pp. 280-284.

(Continued)

*Primary Examiner*—William C Choi
*Assistant Examiner*—Jack Dinh
(74) *Attorney, Agent, or Firm*—Jeffrey B. Powers

(57) ABSTRACT

A fast algorithm is presented which allows for substantially simultaneous acquisition, analysis, and display of a wavefront centroid image, referred to as online aberrometry. A method embodiment involves determination of an average, or most frequently occurring, wavefront aberration over a selected time interval, e.g., 20 sec. Online pupil diameter measurement allows analysis of wavefront aberration as a function of changing pupil size. A wavefront measuring apparatus is disclosed that supports online aberrometry.

20 Claims, 11 Drawing Sheets

OTHER PUBLICATIONS

Hofer H et al., *Dynamics of the Eye's Wave Aberration*, Journal of the Optical Society of America-A, vol. 18, No. 3, Mar. 2001, pp. 497-506.

Sung-Hoon Baik et al., *A New Centroid Detection Algorithm for Shack-Hartmann Wavefront Sensor*, Proceedings of SPIE, vol. 4926, 2002, pp. 251-260.

Prieto P M et al., *Analysis of the Performance of the Hartmann-Shack Sensor in the Human Eye*, Journal of the Optical Society of America-A, vol. 17, No. 8, Aug. 2000, pp. 1388-1398.

I. Miro, N. Lopez-Gil, and P. Artal, *Pupil-Meter and Tracking System Based in a Fast Image Processing Algorithm*, Ophthalmic Technologies IX, SPIE vol. 3591, 1999, pp. 63-70.

Droste D et al., *An ASIC for Hartmann-Shack Wavefront Detection*, IEEE Journal of Solid-State Circuits, vol. 37, No. 2, Feb. 2002, pp. 173-182.

Sophia I. Panagopoulou, Ioannis G. Pallikaris, *Wavefront Customized Ablations with the WASCA Asclepion Workstation*, Journal of Refractive Surgery, vol. 17, Sep./Oct. 2001, pp. S608-S612.

Liang J et al., *Objective Measurement of Wave Aberrations of the Human Eye With the Use of a Hartmann-Shack Wave-Front Sensor*, Journal of the Optical Society of America-A, vol. 11, No. 7, Jul. 1994, pp. 1949-1957.

PCT/EP2004/008205 International Search Report dated Oct. 24, 2005.

PCT/EP2004/008205 Written Opinion of the International Searching Authority dated Oct. 24, 2005.

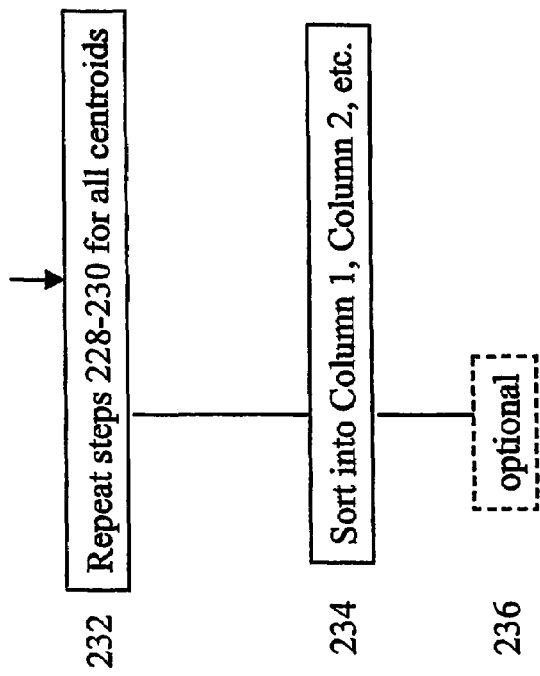
FIG. 4 (con't.)

ONLINE WAVEFRONT MEASUREMENT AND DISPLAY

BACKGROUND OF THE INFORMATION

1. Field of the Invention

Embodiments of the invention are generally directed to the field of image processing, and more particularly to methods and apparatus for the simultaneous measurement, analysis, and display of ocular wavefront information referred to herein as "online" aberrometry.

2. Description of Related Art

There are few technologies that have not been touched by the science of image processing. Advancing development in most fields typically gives rise to process automation where the ability to quickly and accurately detect structures in camera images becomes increasingly important. One area targeted by the embodiments of the instant invention is wavefront aberration measurements of the human eye, although the techniques set forth herein below will find much wider application directed to the detection of structure in images.

The field of ophthalmology concerned with vision correction through refractive surgery, or the use of lens components on or in the eye, has experienced the relatively recent development of aberrometers. These devices allow practitioners to explore the meaning of vision quality and to appreciate that it is not limited merely to visual acuity. Aberrometers which incorporate wavefront sensors can provide information about vision defects that, upon correction, may not only provide visual acuity at the theoretical limit but also better vision, perhaps even customized vision, under a panoply of viewing conditions.

One of the most conventional and well developed forms of ocular wavefront sensing relies on the Hartmann-Shack principle. A Hartmann-Shack wavefront sensor typically includes a microlens array that images various portions of a distorted wavefront exiting the eye onto a CCD detector/camera. The image produced by the microlens array comprises an array of small dots of light that are slightly displaced from reference locations of the light dot image from an unaberrated wavefront. The aberrated dot displacements are related to the localized slopes of the wavefront exiting the eye's pupil. Zernike polynomials (or other mathematical forms) can be derived from these displacements, which are then used to characterize virtually all of the eye's aberrations. The ability to make accurate wavefront calculations is critically dependent upon the true determination of the center location of each dot in the wavefront image. This aspect of the wavefront analysis process is known as centroid detection.

Hartmann-Shack wavefront sensors, and other well-known types such as Tscherning, for example, typically measure single images of centroids or, at best, a very small number of images over a short time interval. The eye, however, is a dynamic system with rapidly varying wavefront changes. The time needed for centroid detection has been the primary culprit hindering real-time measurements with repetition rates greater than a few images per second. A system known in the wavefront art as WASCA has demonstrated a repetition rate of about 7 Hz for the 30-second record of a wavefront. However, the wavefront images must first be recorded, saved, and subsequently evaluated. A single wavefront image requires about 400 Kb of computer memory. Moreover, aberration measurements (e.g., sphere, cylinder/axis, and higher order aberrations) cannot be displayed online, i.e., substantially simultaneously with the wavefront measurement and calculation. Nor is it possible to acquire and save pupil images and centroid images substantially simultaneously, making it virtually impossible to evaluate the influence of eye movement on changes in the wavefront. These illustrations represent some of the exemplary development issues in the field of ocular wavefront measurement addressed by the embodiments of the instant invention.

DETAILED DESCRIPTION OF PREFERRED EMBODIMENTS OF THE INVENTION

Figure 3:
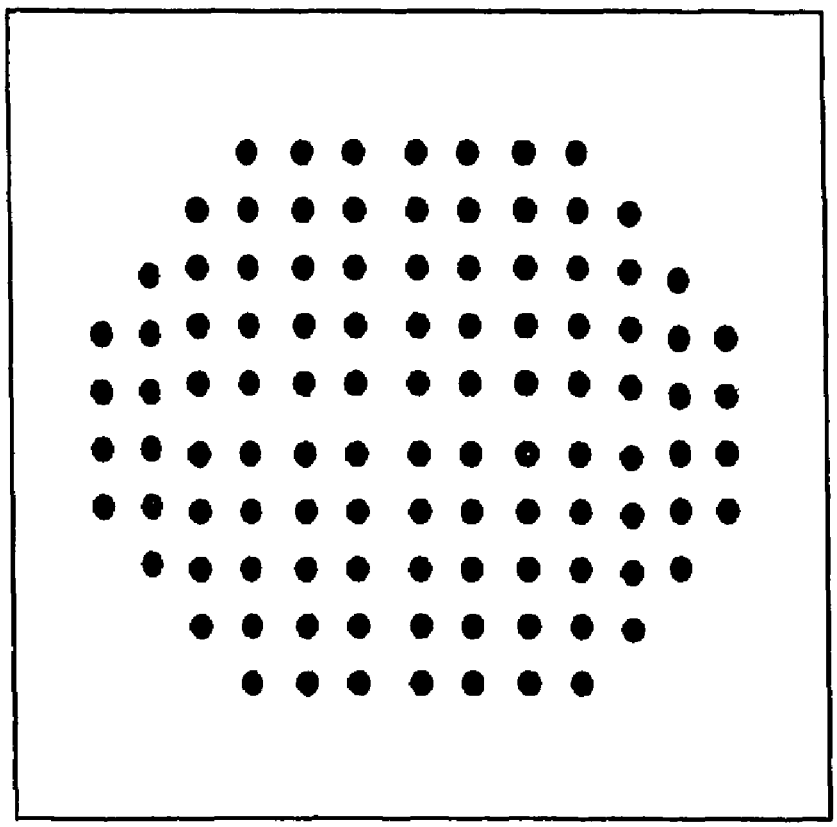
FIG. 3 is a drawing representation of a wavefront (centroid) image associated with an embodiment of the invention.

An embodiment of the present invention is directed to an algorithm that provides for the detection of bright and dark structures in a CCD image. The image may comprise, for illustration purposes only, centroids in a wavefront image, or identified markings on a contact lens surface. FIG. 3 illustrates an array of centroid images 32 as black spots in a simulated Hartmann-Shack wavefront image.

A feature of this embodiment is that the positions of structures such as centroids 32 in a CCD image, for example, can be located and sorted in approximately 5 ms, Zernike coefficients calculated, and wavefront image information displayed in approximately 13 ms or less (utilizing an 800 MHz Pentium® (Intel) processor or equivalent). A 1.6 GHz processor would reduce the total time by approximately one-half by increasing the rate to approximately 50 Hz. The algorithm thus describes what is referred to throughout this description as "online" analysis of wavefront information, referring to the detection, measurement, and display of wavefront information substantially simultaneously at a rate up to approximately 25 Hz.

The embodiments to be described in detail below will be illustrated in terms of a Hartmann-Shack wavefront measurement and analysis, but are more broadly applicable to other wavefront methodologies, for example, those based on the Tscherning principle and others known in the art; however, as noted above, the embodied invention is even more generally applicable to image processing for analyzing structure in a CCD type image.

Figure 1:
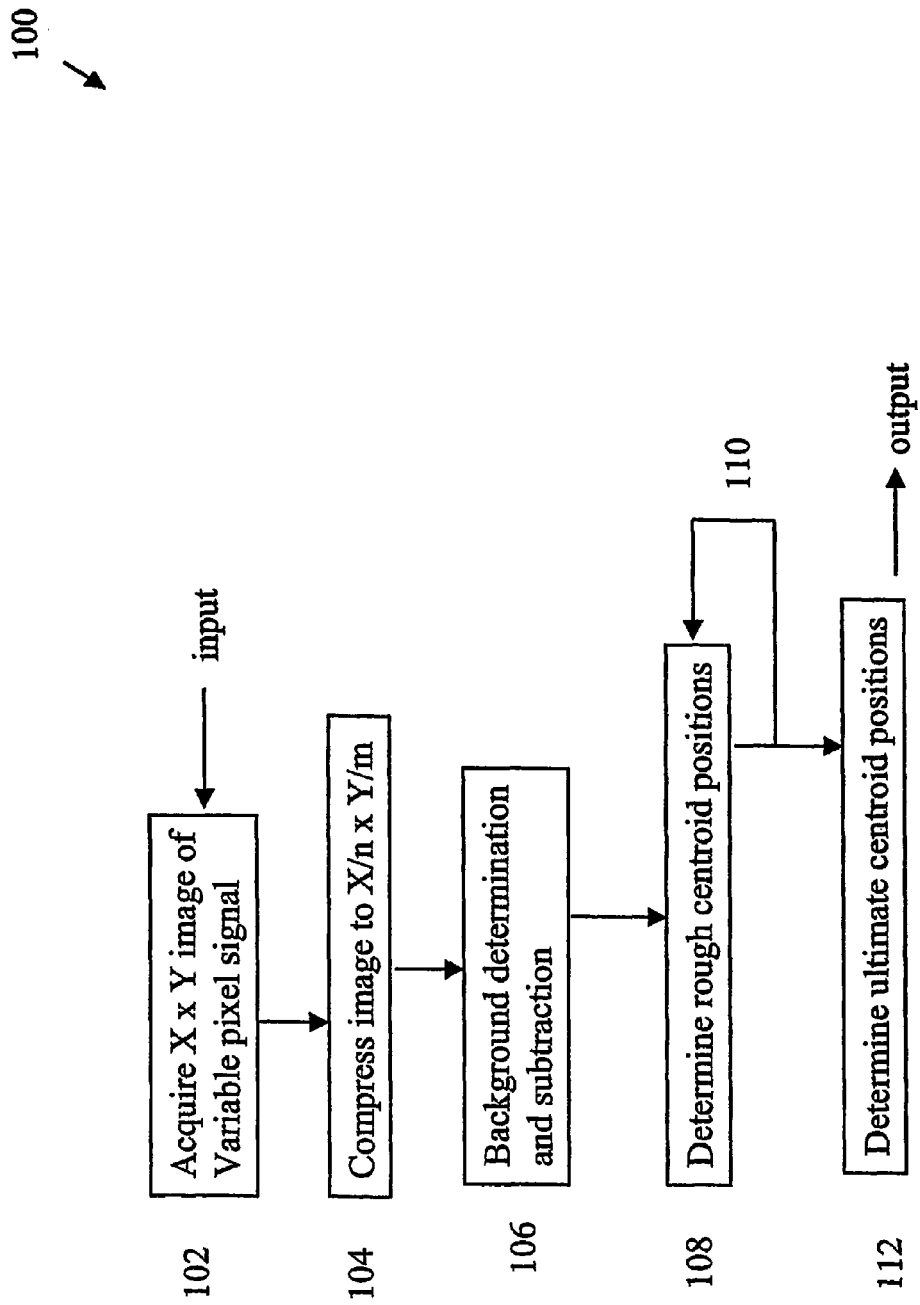
FIG. 1 is a flow chart schematic of a fast centroid detection algorithm embodiment of the invention.

A method for centroid detection in a wavefront image according to the instant embodiment is set forth in the flow chart diagram 100 of FIG. 1. It is noted at the outset that in the illustrated embodiment, a sequential plurality of images are acquired, analyzed, and displayed as desired at a rate of 25 hz, but for the sake of simplicity the algorithm steps set forth below apply to a single wavefront image and are repeated for every wavefront image of the desired sequence.

Figure 2:
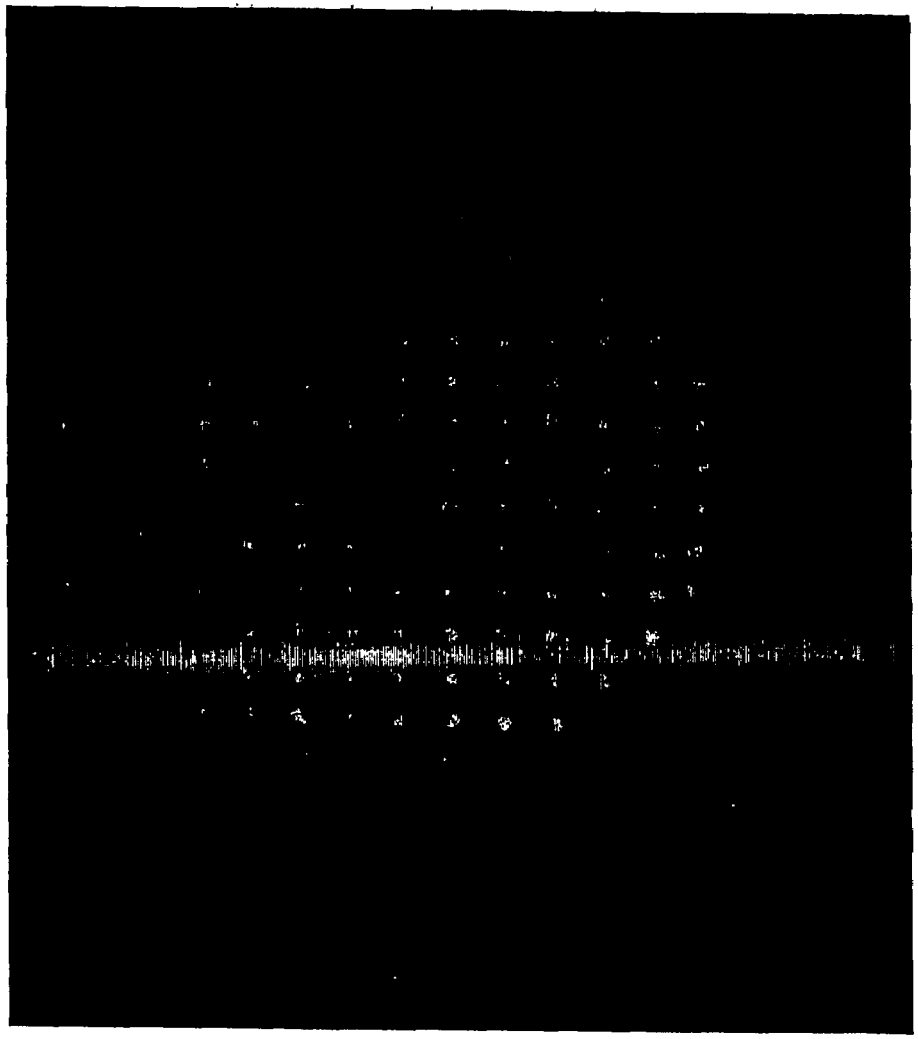
FIG. 2 is a reproduced photographic of a Hartmann-Shack wavefront (centroid) image associated with an embodiment of the invention.

In FIG. 1 at step 102, an X×Y pixel size wavefront image, as shown for example by image 22 in FIG. 2, is acquired. The light spot images are represented by variable pixel signal intensities as shown. Images taken from a CCD camera usually consist of an array of pixels in which every pixel is assigned a number proportional to the amount of charge collected at this pixel. This number is referred to as the signal of the pixel. In the illustrative description that follows, a regular square grid of bright points in a dark image will be described in detail.

i) Image Compression

After acquiring the image at step 102, the image is compressed from size X×Y pixels to X/n×Y/m pixels at step 104. This can be done by averaging the signal for every pixel in an n×m pixel square in the original image starting, for example, in the upper left corner of the image and scanning through the image. The signal in the upper left corner of the compressed image is then set to the average of the first square, the signal of the next pixel is set to the average of the next (second) square, and so on, finally yielding a picture X/n×Y/m pixels in size. n and m should be integers with X/n and Y/m also being integer values. In an exemplary embodiment, n=m=8.

ii) Background Subtraction

At step 106, the compressed image is then divided into square regions, or tiles (not to be confused with the pixel squares in (i) above). In the exemplary embodiment, one tile is a square of 64×64 pixels, but other sizes can be used. Typically, one tile might contain 3-5 centroids. The average signal is again calculated for every tile. The average values for the tiles are then linearly extrapolated to yield a background value for any location in the image. This background is then subtracted from the image yielding a low signal outside the centroids. In the illustrative embodiment, a signal-to-noise ratio of two was improved to a signal-to-noise ratio of 10 by the background subtraction.

iii) Rough Structure Detection

At step 108, the approximate, or rough, structure points (centroids) are identified. First, a maximum is defined as the highest signal in the compressed image. The maximum is determined by a scan through the image, and the X-position, Y-position, and signal value of every pixel is recorded in a table, but only if the signal value of this point is greater than a certain percentage of the maximum, e.g., 30% (other values can be selected by the user). In the exemplary embodiment, this yields a table (Table I) of about 400 entries. The table is sorted by descending signal as shown. Any of a variety of quick sorting routines is available to accomplish this.

TABLE I

| Signal | X Position | Y Position |
|--------|------------|------------|
| 223 | 86 | 55 |
| 154 | 85 | 75 |
| 135 | 87 | 95 |
| 133 | 115 | 56 |
| 110 | 118 | 74 |
| 108 | 114 | 93 |
| . | . | . |
| . | . | . |
| . | . | . |

The first entry (highest signal value) is defined as the first rough structure point. Then, all entries in the table that obey a certain pre-set condition are defined as rough structure points. In the exemplary embodiment, the pre-set condition is that the position of the particular entry is farther away from all yet found rough structure points than a pre-set distance. In an exemplary embodiment, the distance is 17 pixels. After this first iteration, a table of rough structure points is created that includes approximately 95% of all points that are to be detected.

iv) Refine Detection of Structure

To increases the confidence level that all points of the structure are found, step 108 can be repeated as shown at block 110, setting a new minimum to a certain percentage of the minimum in the first iteration. The second iteration finds points that were too weak in signal to be found in the first iteration. The rough structure points found in the first iteration are accounted for so they will not be found again (i.e., they do not obey the condition of being farther away than a pre-set distance from the detected points).

v) Ultimate Structure Detection

At step 112, the ultimate centroid positions are determined. Since the image was earlier compressed in step 104, much of the information originally contained in the image was ignored. This information can now be used to determine more exact centroid positions. Using the original uncompressed image, a square of, for example, 15×15 pixels is created around every rough point. Generally, each square is smaller than 2× the minimum distance to insure that each square contains only one centroid, and is larger than the centroid itself. In the exemplary embodiment this value is between five and 30 pixels. Then, the center of mass of signal for the signal distribution inside the square is determined, giving rise to the substantially exact position of the centroid.

In an aspect of the embodiment, step 112 can be repeated, for example, 1, 2, 3 . . . n times to determine still more exact results. The calculated center of mass in the previous step is subsequently used. Each structure point can also be assigned a quality factor depending on how much the position of the center of mass changes if the square around the pixel is willingly shifted by a user-set distance, at step 112. In an exemplary embodiment, this distance is five pixels. The points whose positions have changed the least are assigned the highest quality factors. In this manner, spurious points or noise assigned a low quality factor can be eliminated, as they likely represent false structure points.

Figure 4:
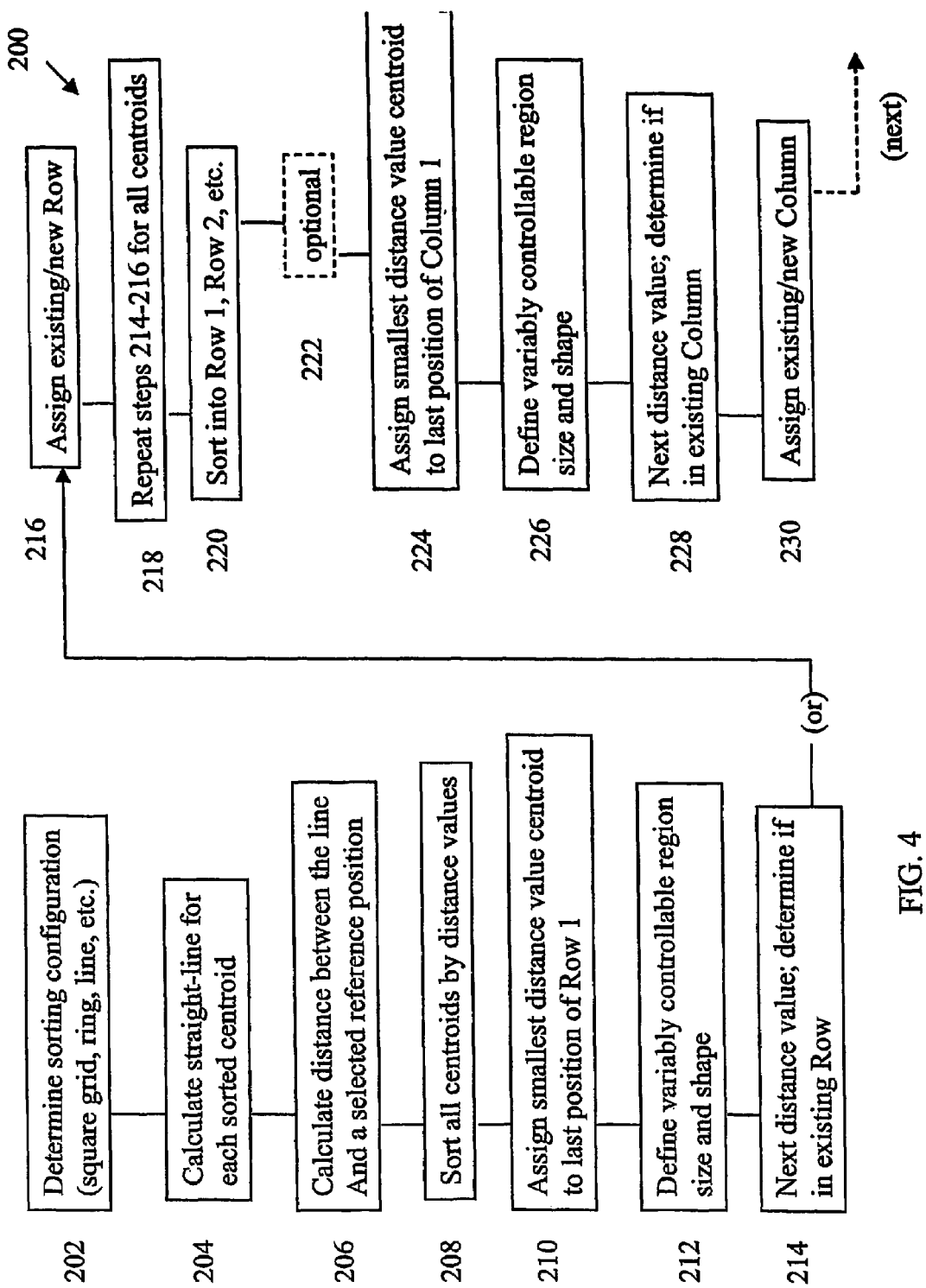
FIG. 4 is a flow chart schematic of a sorting algorithm according to an embodiment of the invention.

In the illustrative embodiment directed to Hartmann-Shack wavefront sensing, it is desirable to be able to correlate the centroids with the corresponding image forming lenslet of the microlens array. Thus, an aspect 200 of the embodiment as illustrated in FIG. 4 is directed to the process of sorting the detected centroids so as to assign them to a regular square grid pattern. It will be appreciated by those skilled in the art that the algorithm can be easily adapted to other structures or configurations such as, for example, points on rings, or any straight line of points.

Figure 5:
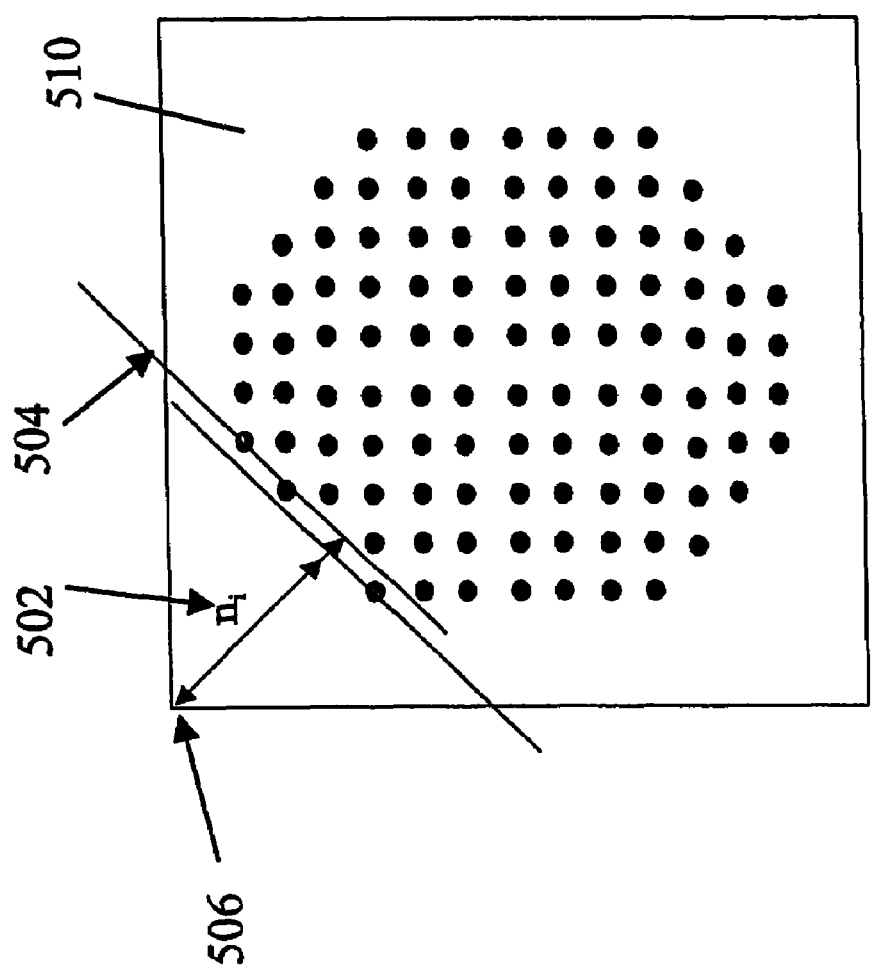
FIG. 5 is another drawing representation of a wavefront (centroid) image representing an algorithm process according to an embodiment of the invention.
Figure 6:
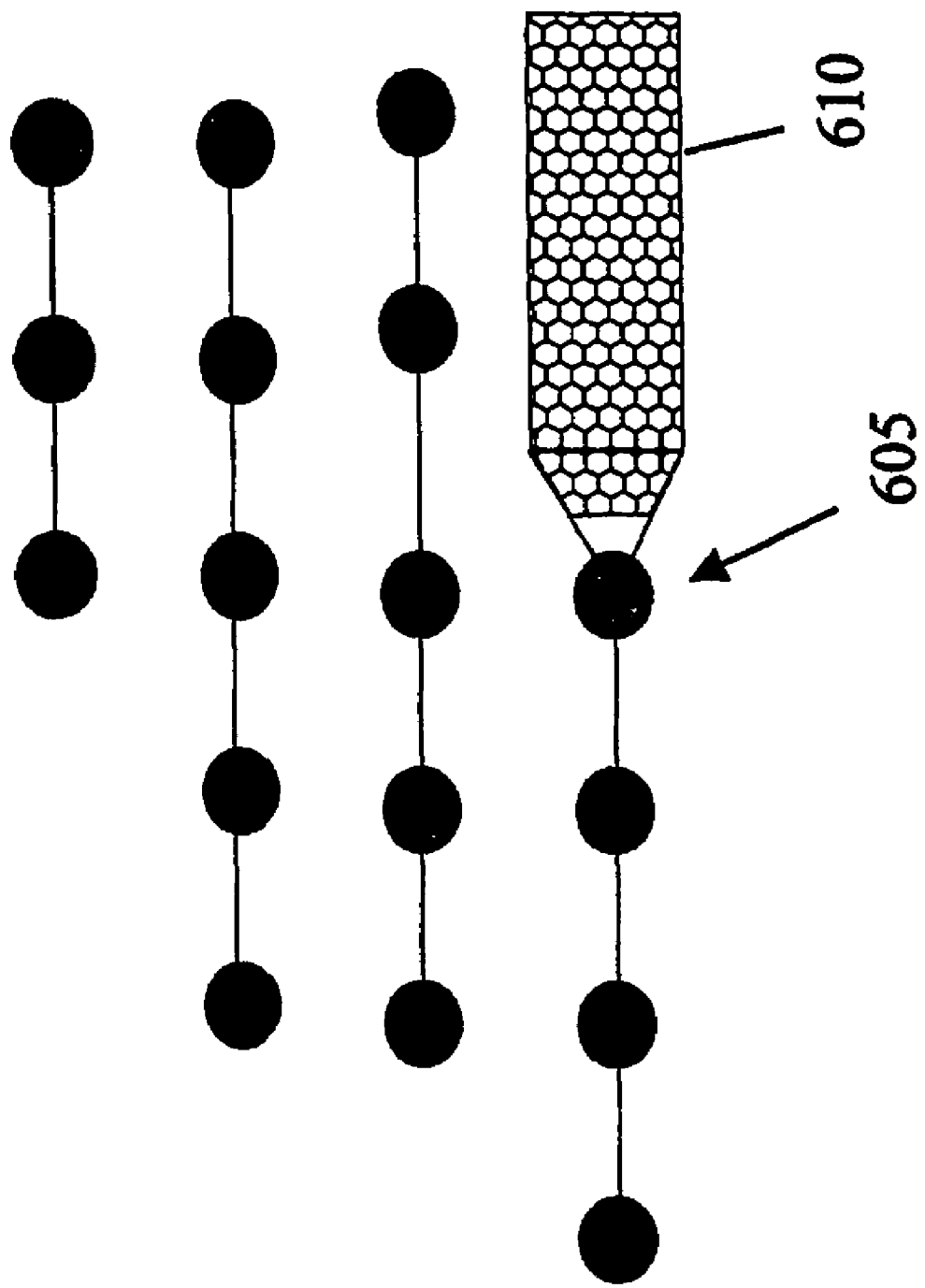
FIG. 6 is a schematic illustration representing another algorithm process according to an embodiment of the invention.
Figure 7:
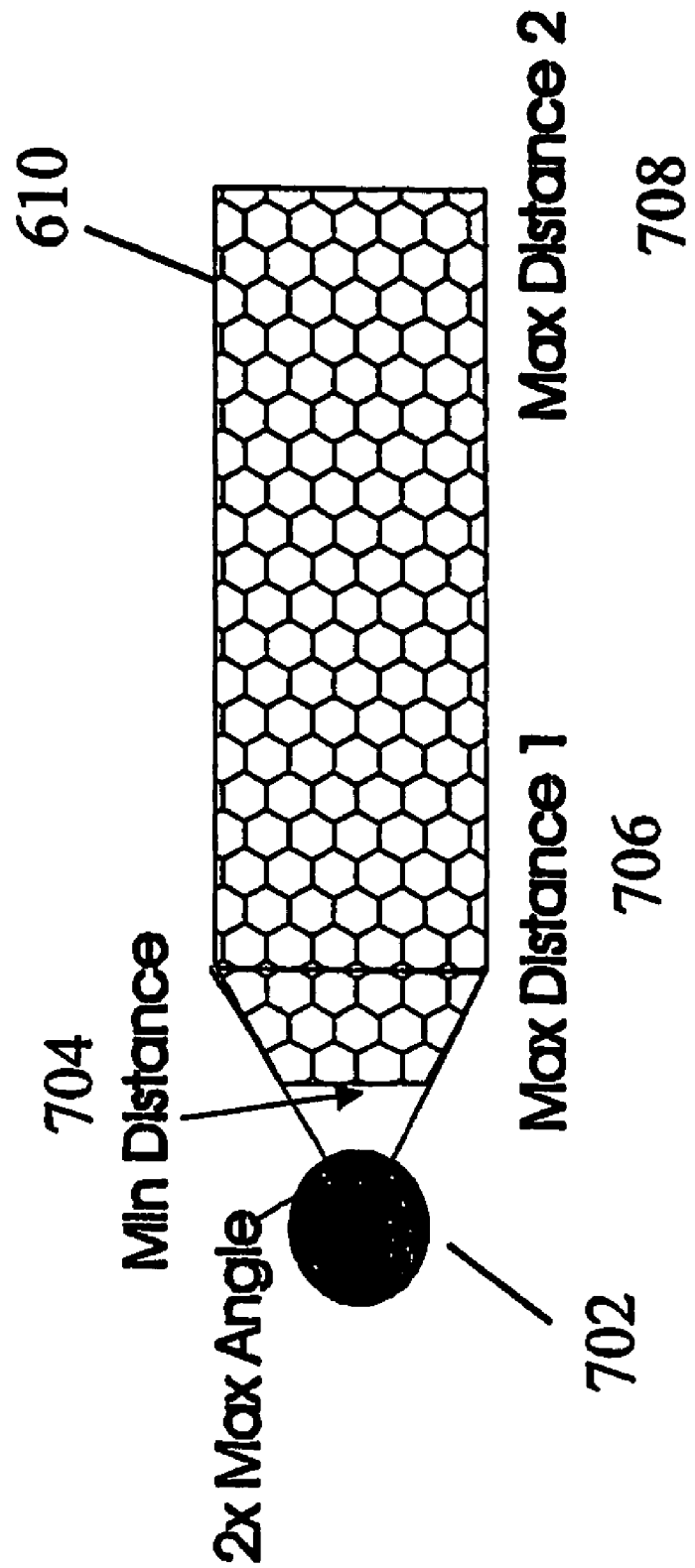
FIG. 7 is an illustration representing another algorithm process according to an embodiment of the invention.

At step 202, the desired sorting configuration is selected. In the exemplary embodiment, the configuration is a square grid based upon the geometry of the microlens array. For every previously found centroid point, i, the formula for a straight line is calculated containing the centroid point, i, and having a slope of 1 (45°), as shown at step 204. For starting positions of the upper left corner or lower right corner of the image, slope values between 0.1 to 0.9 can be used. Likewise, when the starting position is the upper right corner or the lower left corner of the image, slope values from −0.1 to −0.9 can be selected. At step 206, the distance 502 ($n_i$), between the line 514 and, in the illustrative embodiment, the upper left corner 506 of the image 510 is calculated, as illustrated in FIG. 5. All centroids, i, are then sorted by $n_i$ at step 208 starting with the centroid having the smallest $n_i$ value. At step 210, the centroid with the smallest $n_i$ value is assigned to Row 1 and is stored in memory as the last centroid of Row 1. In an aspect of the embodiment, the last centroids of the existing rows are stored in memory during step 210. At step 212, a region 610 is defined that, in an exemplary embodiment, comprises an area to the right of the last centroid 605 of a given row, having dimensions that can be controlled and varied by parameters of the lenslet array, and having a shape that is suited to detecting the selected grid configuration, as illustrated in FIG. 6, which shows the search area 610 for the next centroid. Any shape suited for detecting other grid configurations is alternatively possible. Examples of the lenslet array parameters include maximum angle 702, minimum distance 704, maximum distance 1 (706), and maximum distance 2 (708), as illustrated in FIG. 7. Then, at step 214, the next higher $n_i$ value is selected and that centroid is checked, with respect to all existing rows, whether the centroid is in the defined region. If yes, then at step 216, that centroid is assigned as the last centroid of that row. If no, than that centroid is assigned the last centroid of a new row. Steps 214-216 are now repeated for all centroids. In this manner, rows start to build up from left to right. At step 220, the average y-position for each row is calculated and the rows are sorted according to their average y-position. This step facilitates marking of the top row as Row 1, the next row as Row 2, and so on.

Figure 8:
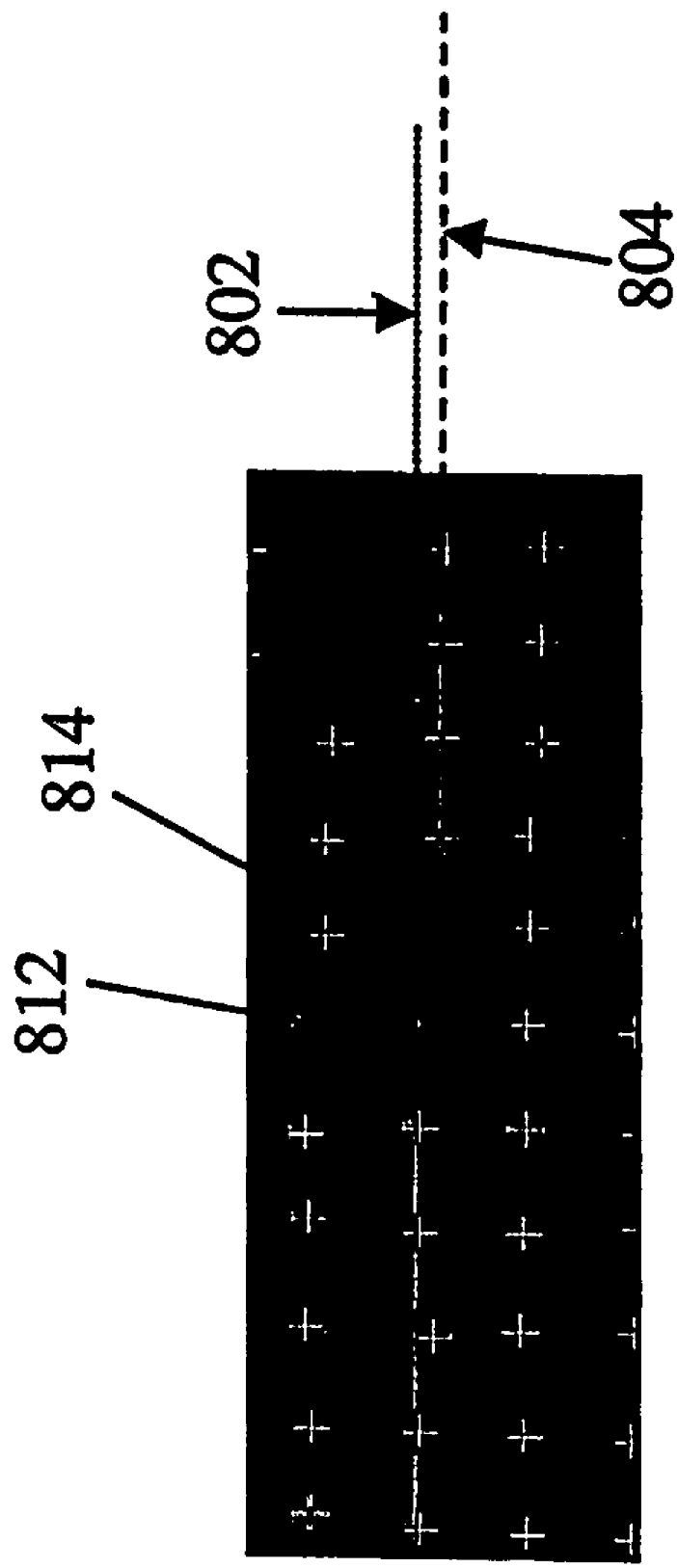
FIG. 8 is a reproduced photographic of part of a Hartmann-Shack wavefront (centroid) image representing another algorithm process according to an embodiment of the invention.

Before describing the steps for sorting the columns, it is beneficial to point out that the situation can occur as illustrated by the faintly seen points lying along lines 802, 804 as shown in FIG. 8; i.e., some centroids 812, 814 in the middle of a row have not been detected due to bad quality of the centroid points, and the centroids to the left and right have been assigned to different rows. In this event, optional step 222 involves merging these rows. This is accomplished by the following sub-steps: From the mean average y-position for each row from step 214, calculate the mean distance between the rows by subtracting $y_{row1}-y_{row2}$ (yielding the distance between Row1 and Row2); $y_{row2}-y_{row3}$ (yielding the distance between Row2 and Row3); and so on, and then taking the mean values of the obtained distances. In the exemplary embodiment, the criteria for merging rows j and k is: If $y_j-y_k<f*a$ and $(P_{k,first}>P_{j,last}$ or $P_{k,last}<P_{j,first})$, where:

f is a variable parameter in the range between about 0.1-0.7, that is set by the user. In the exemplary embodiment, values between 0.3 to 0.5 are used;

a is the mean distance between rows (see above);

$P_{k,first}$ is the x value of the first (left-most) centroid of the k row; and $P_{k,last}$ is the x value of the last (right-most) centroid of the k row.

In other words, the rows are merged if they are much closer in the y-position than typical and if they don't overlap i.e. row j is either completely to the left or completely to the right of row k.

The process for sorting the columns begins at step 224 where the list of sorted centroids by distance value from step 208 is used again. The centroid with the smallest $n_i$ is assigned to Column 1 and is stored in memory as the last centroid of Column 1. In an exemplary aspect, the last centroids of an existing column are always stored in memory during step 224. At step 226, a region is defined that, in the exemplary embodiment, comprises an area below the last centroid of a given column having dimensions and shape that are controlled and varied by the same parameters of the lenslet array as set forth above. This is illustrated by tilting the diagram in FIG. 6 downward by 90 degrees. At step 228, the next higher $n_i$ value is selected and that centroid is checked, with respect to all existing columns, whether the centroid is in the defined region. If yes, then at step 230, that centroid is assigned as the last centroid of that column. If no, than that centroid is assigned the last centroid of a new column. Steps 228-230 are now repeated for all centroids. In this manner, columns start to build up from top to bottom. At step 234, the average x-position for each column is calculated and the columns are sorted according to their average x-position. This step facilitates marking of the left-most column as Column 1, the next column as Column 2, and so on.

The situation can occur, as mentioned above with reference to FIG. 8, where some centroids in the middle of a column have not been detected due to bad quality of the centroid points, and thus the centroids above and below have been assigned to different columns. In this event, optional step 236 involves merging these columns. This is accomplished by the following sub-steps: From the mean average x-position for each column from step 228, calculate the mean distance between the columns by subtracting $x_{column1}-x_{column2}$ (yielding the distance between Column1 and Column2); $x_{column2}-x_{column3}$ (yielding the distance between Column2 and Column3); and so on, and then taking the mean values of the obtained distances. In the exemplary embodiment, the criteria for merging columns j and k is: If $x_j-x_k<f*a$ and $(P_{k,first}>P_{j,last}$ or $P_{k,last}<P_{j,first})$, where:

f is a variable parameter in the range between about 0.1-0.7, that is set by the user. In the exemplary embodiment, values between 0.3 to 0.5 are used a is the mean distance between columns;

$P_{k,first}$ is the y value of the first (top-most) centroid of the k column; and $P_{k,last}$ is the y value of the last (bottom-most) centroid of the k column.

In other words, the columns are merged if they are much closer in the x-position than typical and if they do not overlap; i.e. column j is either completely above or completely below column k.

From the sorted centroid positions, a Zernike calculation can be made to determine the wavefront aberration. According to the illustrated embodiment, the processes for acquiring a single image and displaying the wavefront aberration information, using an 800 MHz Pentium processor, are listed below with their corresponding processing times:

| | |
|---|---|
| Finding and sorting the centroids: | ~5 ms; |
| Performing the Zernike calculations: | ~5 ms; |
| Imaging operations: | ~8 ms; |
| Image display: | ~8 ms |
| Pupil coordinate location (optional): | ~6-8 ms; |
| Contact lens position (optional): | ~5 ms |

In an illustrative aspect of the embodiment, the Zernike calculation process is performed twice during a measurement cycle, once for the second-order terms and once for the higher-order terms. The total time per image is approximately 40 ms or slightly less at a repetition rate of 25 Hz. In contrast, conventional real-time (as opposed to online) wavefront analysis consists of storing a sequence of images and subsequently-analyzing the images for wavefront information. These techniques are limited by computer storage requirements. For example, storing two images at 25 Hz for 30 seconds requires approximately 400 MB/measurement. On the other hand, according to the illustrative embodiment, the storage of images is not necessary because the information contained in those images has already been extracted by detecting the centroid and pupil position. Storing only pupil and centroid position data results in data storage requirements of only about 700 Kb of memory for a 20 second measurement at 25 Hz, which will yield 500 images.

Another embodiment of the invention is directed to a device-readable medium that has stored thereon an executable instruction for carrying out the algorithm described above. Appropriate media are well known and include, without limitation, CD, DVD, diskette, hard drive, carrier wave, and others.

Figure 9:
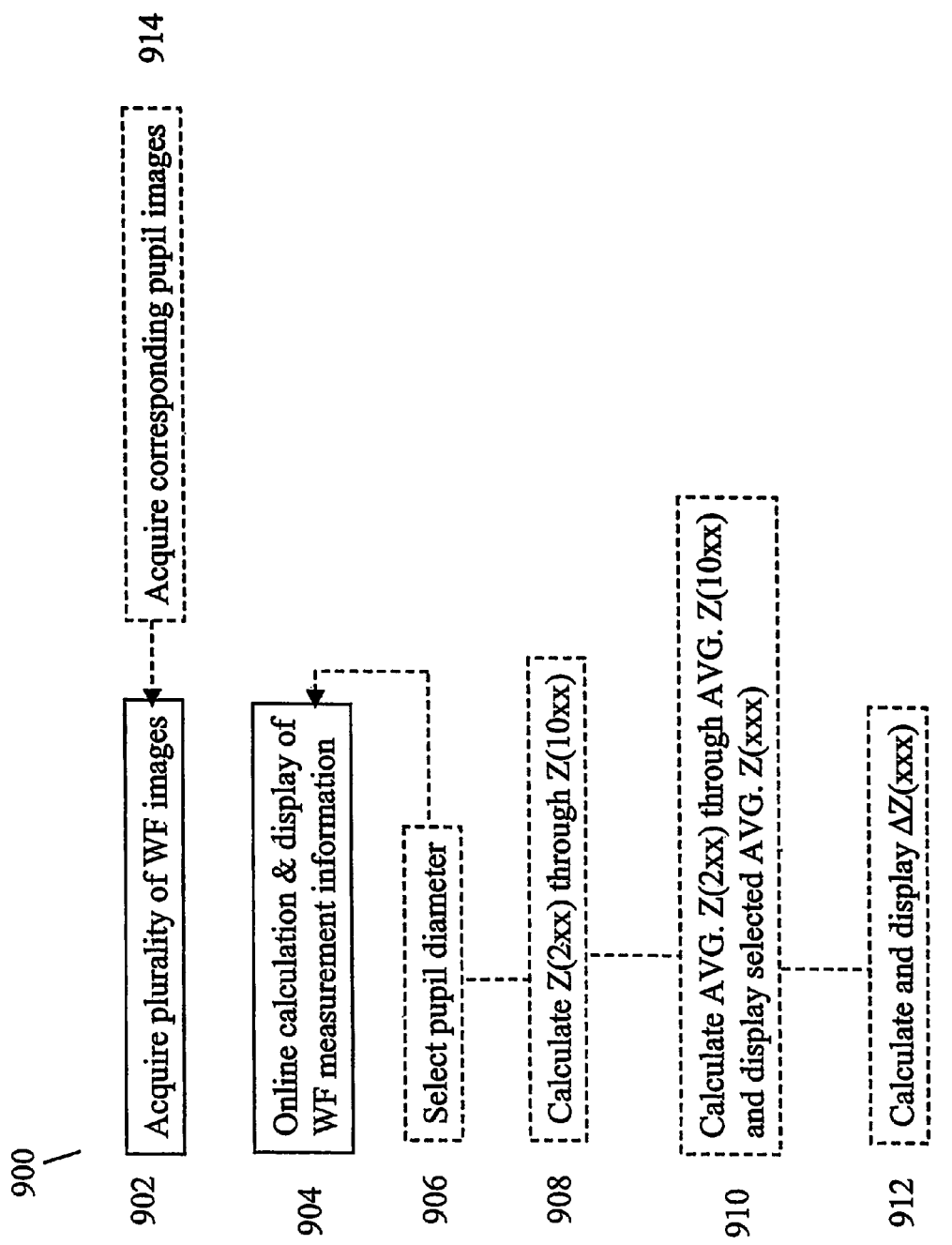
FIG. 9 is a flow chart schematic directed to another embodiment of the invention.

Another embodiment of the invention is directed to a method for wavefront analysis. The method is set forth in the block diagram of FIG. 9. The method comprises at step 902 acquiring a plurality of wavefront images of light exiting a pupil of an eye, where each of the images includes a displaced centroid that is indicative of wavefront measurement information of the eye, and at step 904 calculating and displaying the wavefront measurement information online for a selected aberration order. As used hereinabove and throughout the description, the term "online" refers to the substantially simultaneous measurement, analysis, and display of the wavefront measurement information. The exemplary fast algorithm described in the previous embodiment is but one way to facilitate an online process. Persons skilled in the art will appreciate that other algorithms can be developed, or are currently available, that will also facilitate the online technique.

In an aspect of this embodiment, the images are acquired at a rate equal to or greater than 10 Hz. In an exemplary aspect the images are obtained at a rate of 25 Hz; however, computer processor speed is the limiting factor in the image acquisition rate. In another aspect, at least 50 sequential images are acquired. In another aspect, the step 906 of calculating and displaying the wavefront measurement information online for a selected aberration order is performed for a selected pupil diameter. That is to say, if a pupil diameter value is not selected prior to the measurement, the display will be limited to second order aberrations (sphere or spherical equivalent, and cylinder/axis) because second order aberrations are pupil diameter independent. However, one may want to insure that the resultant wavefront information is interpreted for a substantially constant pupil diameter, or a controlled variation in pupil diameter. On the other hand, a pupil diameter value can be selected prior to measurement allowing any Zernike order (e.g., coma, spherical aberration, higher-orders) for that given diameter to be displayed online. An exemplary range of pupil diameters is between about 2 mm to 10 mm.

In an exemplary embodiment, at a repetition rate of 25 Hz, 500 images can be obtained (and thus 500 measurements can be made) over a 20-second time interval. The first 125 images might be obtained for pupil diameter, $D<D_{min}$; the next 250 images for $D_{min} \leq D \leq D_{max}$; and the remaining 125 images for $D_{max}<D$. Using the set of 250 images, Zernike amplitudes for $Z_{2xx}$ through $Z_{10xx}$ can be calculated as set forth at step 908. If desired, at step 910 an average value of a selected Zernike order can be calculated and displayed online. If an average value has been calculated, well known statistical techniques can be used to determine a standard deviation at step 912 that provides an error band for the average wavefront measurement. In an aspect of this embodiment, blinking periods can be determined which contain anomalous wavefront information, and the information during these blinking periods discarded. Likewise, if contact lens position were being measured, for example, it would be advantageous to eliminate measurements during blinking periods as lens settlement takes a short time to occur. Knowing the value of the most frequently occurring wavefront amplitude for a particular aberration order based upon pupil diameter will allow the practitioner to prescribe a treatment or vision correction resulting in optimum vision for the patient.

In a related aspect according to this embodiment, at step 914 a sequence of pupil images corresponding to the wavefront images can also be obtained. These images can be saved simultaneously so that the influence of eye movement on changes in the wavefront can be evaluated.

Figure 10:
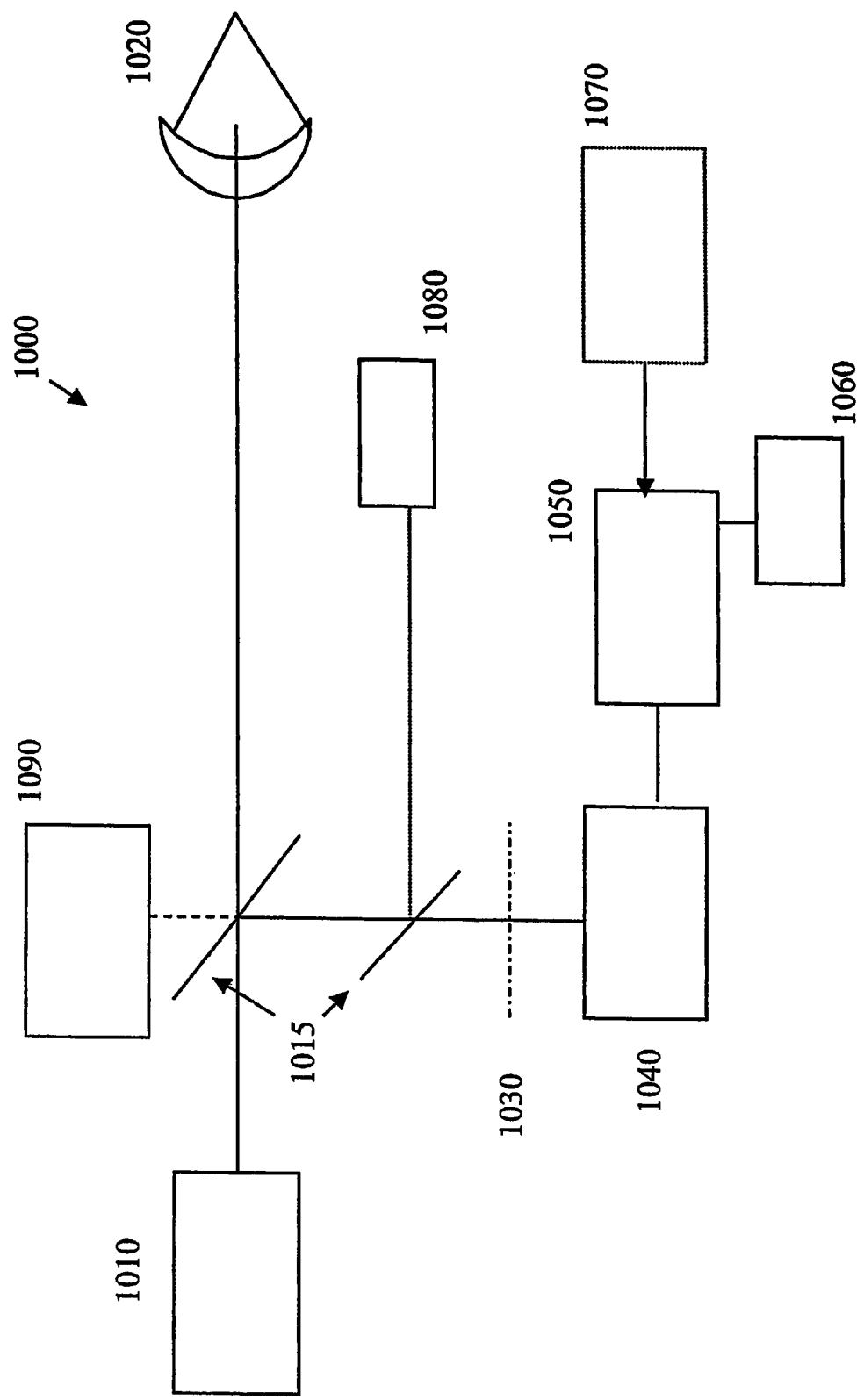
FIG. 10 is a block diagram of an apparatus embodiment of the invention.

Another embodiment of the invention is directed to a wavefront measuring apparatus 1000 illustrated by the block diagram in FIG. 10. The apparatus includes an illumination component 1010 that delivers a small spot of light onto the retina of the eye 1020, an imaging component 1030 that forms a centroid image of the illumination light scattered from the retina and exiting the pupil of the eye, a detector 1040 adapted to acquire the centroid image, a processor 1050 working in cooperation with the detector that executes a centroid displacement calculation to determine the wavefront measurement information, a display component 1060 operatively connected to the processor that displays a selected wavefront measurement information, and means 1070 for instructing an online calculation and display of the selected wavefront measurement information. An optional pupil camera 1080 and pupilometer 1090 is also shown, where components 1015 are beam splitters or optical equivalents thereof.

We claim:

1. A method for centroid detection in an image, comprising:
    a) acquiring an X×Y size image represented by a variable pixel signal intensity;
    b) compressing the X×Y size image to an X/n×Y/m size image, where n, m equal any integers and X/n, Y/m are integer values;
    c) determining a background intensity for any position in the compressed image and subtracting this background from the compressed image;
    d) detecting a plurality of approximately positioned centroids in the background-subtracted compressed image;
    e) iterating step (d) until approximate positions of a desired plurality of centroids are detected;
    f) converting the approximate position of the desired plurality of centroids into more exact positions in the X×Y size image,
    whereby every centroid position in the image has been identified;
    g) iterating step (f) until a desired level of more exact positions is determined; and
    h) assigning a quality factor to each centroid in relation to a magnitude of positional change for each centroid in each iteration of step (g).

2. The method of claim 1, comprising:
    sorting the centroids determined from step (f) according to a predetermined configuration.

3. The method of claim 2, wherein the configuration is a geometric grid.

4. The method of claim 3, comprising a rectangular grid.

5. The method of claim 4, comprising:
a) calculating a straight line formula for each sorted centroid, i, containing the centroid point, i, and having a slope between the values of about $<-0.1$ or $>0.1$;
b) calculating a distance, ni, between the line and a reference position in the image;
c) sorting all centroids, in, by ni starting with the smallest ni value;
d) assigning the centroid with the smallest ni to a first row and storing this centroid as a last centroid in the first row;
e) defining a region as an area to the right of a last centroid of a given row having dimensions that are variably controllable by an imaging component parameter and a shape suitable for detection of a selected grid structure;
f) obtaining the next ni value and determining, for all existing rows, whether the centroid is within the region;
g) assigning the centroid as the last centroid in the given row if the centroid is within the region, or, assigning the centroid as the last centroid in a new row if the centroid is outside the region;
h) repeating steps (f-g) for all centroids;
i) calculating an average y-position for each row and sorting the rows according to the average y-positions to identify a top row, Row 1, a next row, Row 2, and so on to Row n;
j) assigning the centroid with the smallest ni to a first column and storing this centroid as a last centroid in the first column;
k) defining a region as an area below the last centroid of a given column having dimensions that are variably controllable by the imaging component parameter and a shape suitable for detection of the selected grid structure;
l) obtaining the next ni value and determining, for all existing columns, whether the centroid is within the region;
m) assigning the centroid as the last centroid in the given column if the centroid is within the region, or, assigning the centroid as the last centroid in a new column if the centroid is outside the region;
n) repeating steps (l-m) for all centroids; and
o) calculating an average x-position for each column and sorting the columns according to the average x-positions to identify a first column, Column 1, a next column, Column 2, and so on to Column n.

6. The method of claim 5 wherein the reference position is an upper left corner of the image.

7. The method of claim 2, wherein the configuration is a ring.

8. The method of claim 2, wherein the configuration is a straight line.

9. The method of claim 2, comprising:
associating each determined centroid with a respective centroid image forming element.

10. The method of claim 1, wherein compressing the X×Y size image to an X/n×Y/m size image comprises:
a) averaging the signal for every pixel in an n×m square staffing in a first predetermined region of the original image and scanning through the image, setting a signal level in a corresponding first predetermined region of the compressed image to the average value of the first predetermined region;
b) repeating step (a) for a second and subsequent predetermined regions until the X/n×Y/m image size is obtained.

11. The method of claim 10, wherein n=m=8.

12. The method of claim 10, wherein the first predetermined region is the upper left corner of the image.

13. The method of claim 1, wherein step (c) comprises:
dividing the compressed image into a plurality of image segments each of which contains a plurality of centroids, determining an average signal value for each image segment, and extrapolating the average values for each image segment to determine the background intensity level.

14. The method of claim 13, wherein the image segments are squares.

15. The method of claim 13, wherein each image segment contains approximately 3 to 5 centroids.

16. The method of claim 1, wherein step (d) comprises:
a) determining a maximum signal value in the image;
b) setting a threshold value as a predetermined percentage of the maximum;
c) determining an X-position, a Y-position, and a signal strength of each pixel that has a signal strength greater than the threshold value;
d) sorting the values from step (c) in descending order of signal strength;
e) assigning the highest signal strength as first approximately positioned centroid; and
f) selecting a pre-set condition for defining all sorted values as approximately positioned centroids, which obey the pre-set condition.

17. The method of claim 16, wherein the pre-set condition is that the position of each subsequent approximately positioned centroid is a farther distance away than a pre-set distance from all yet determined approximately positioned centroids.

18. The method of claim 17, further comprising setting a new threshold value to a predetermined percentage of a minimum value of the sorted signal strengths and iterating steps (c-f), wherein the already identified approximately positioned centroids are not identified again.

19. The method of claim 1, wherein step (I) comprises:
defining a boundary structure around every approximate position of the desired plurality of centroids in the original image; and
determining a center of mass of the signal for the signal distribution inside of the boundary.

20. A device readable medium having stored thereon an executable instruction in the form of the method of claim 1.

* * * * *